(12) United States Patent
Tipping et al.

(10) Patent No.: US 9,895,175 B2
(45) Date of Patent: Feb. 20, 2018

(54) METHOD, SYSTEM, AND APPARATUS FOR BREAKING BONY SEGMENT IMPLANT EXTENSION

(71) Applicant: Osseus Fusion Systems, LLC., Dallas, TX (US)

(72) Inventors: Chase D. Tipping, Dallas, TX (US); Thomas Loftus, Austin, TX (US)

(*) Notice: Subject to any disclaimer, the term of this patent is extended or adjusted under 35 U.S.C. 154(b) by 45 days.

(21) Appl. No.: 14/989,791

(22) Filed: Jan. 6, 2016

(65) Prior Publication Data
US 2017/0150999 A1 Jun. 1, 2017

Related U.S. Application Data

(60) Provisional application No. 62/261,404, filed on Dec. 1, 2015.

(51) Int. Cl.
*A61B 17/70* (2006.01)

(52) U.S. Cl.
CPC .............................. *A61B 17/7074* (2013.01)

(58) Field of Classification Search
CPC ........................ A61B 17/7074; A61B 17/8863
See application file for complete search history.

(56) References Cited

U.S. PATENT DOCUMENTS

| | | | |
|---|---|---|---|
| 8,262,662 B2 | 9/2012 | Beardsley et al. | |
| 8,388,659 B1* | 3/2013 | Lab .................... | A61B 17/7037 606/265 |
| 2006/0074445 A1* | 4/2006 | Gerber ............... | A61B 17/7074 606/191 |
| 2008/0300638 A1* | 12/2008 | Beardsley .......... | A61B 17/7032 606/306 |

* cited by examiner

*Primary Examiner* — Julianna N Harvey
(74) *Attorney, Agent, or Firm* — Merle W Richman, Esq.; CKR Law

(57) ABSTRACT

Embodiments of a bony implant extension arm breakoff tool are described. The tool may enable a surgeon to break a section of a bony segment implant extension located in a transdermal location within a patient. Other embodiments may be described and claimed.

13 Claims, 11 Drawing Sheets

SECTION D

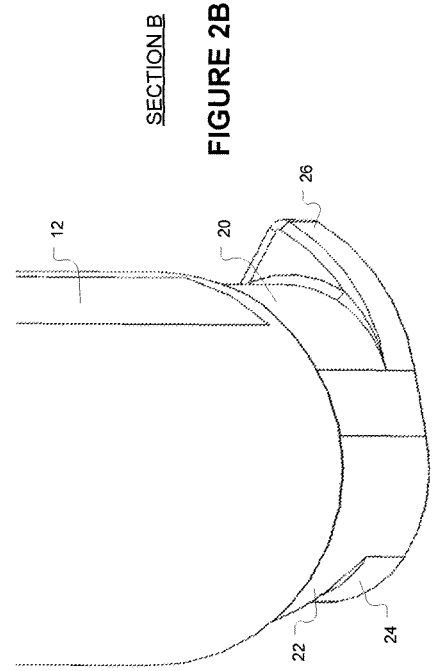
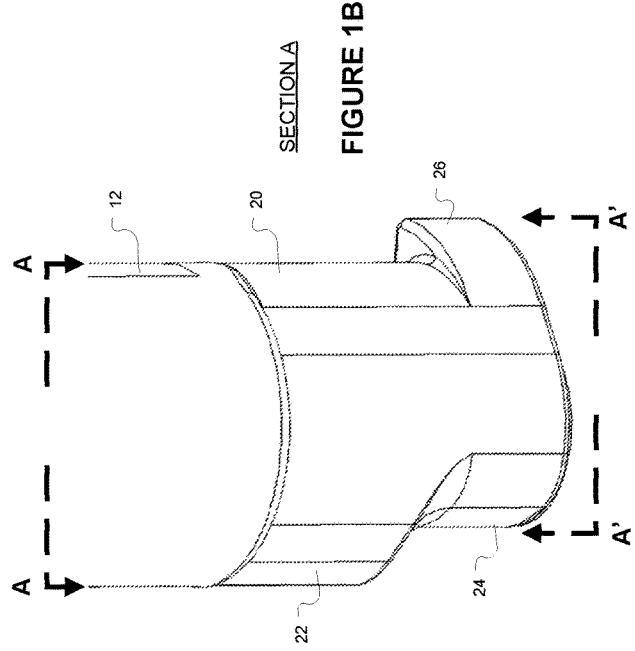
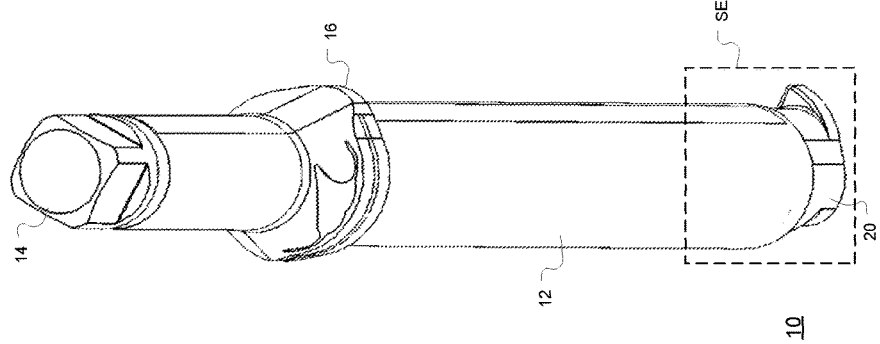
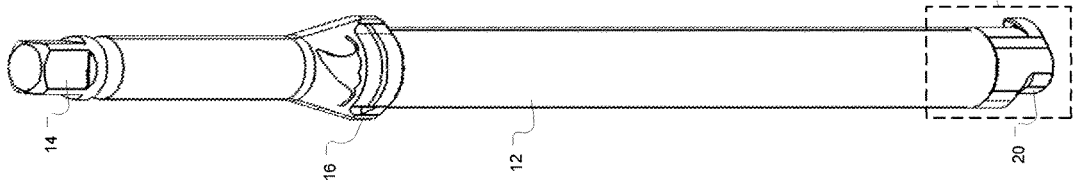

SECTION C

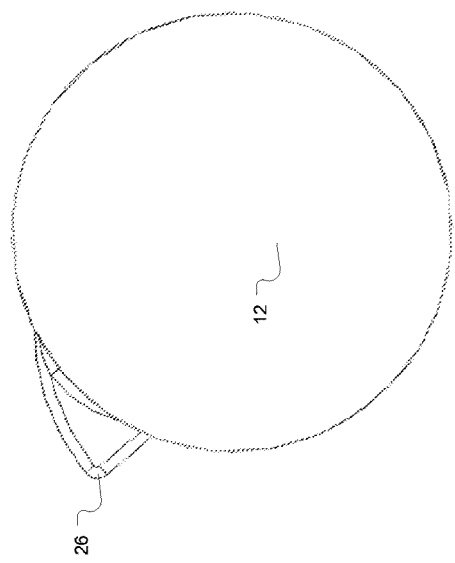
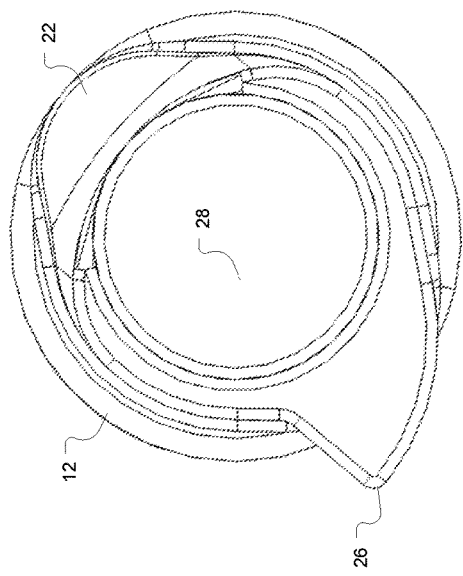
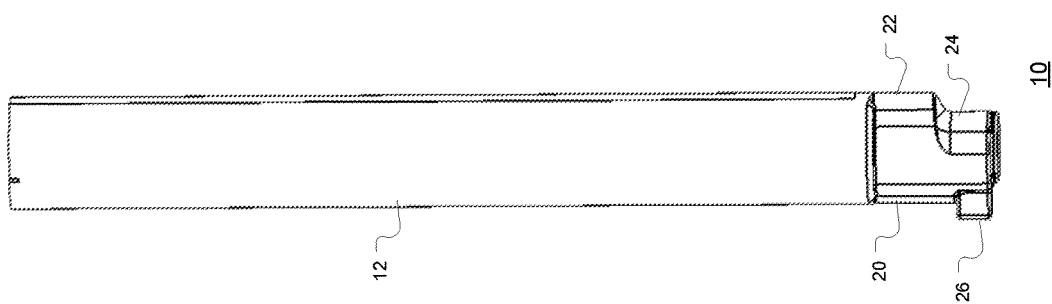

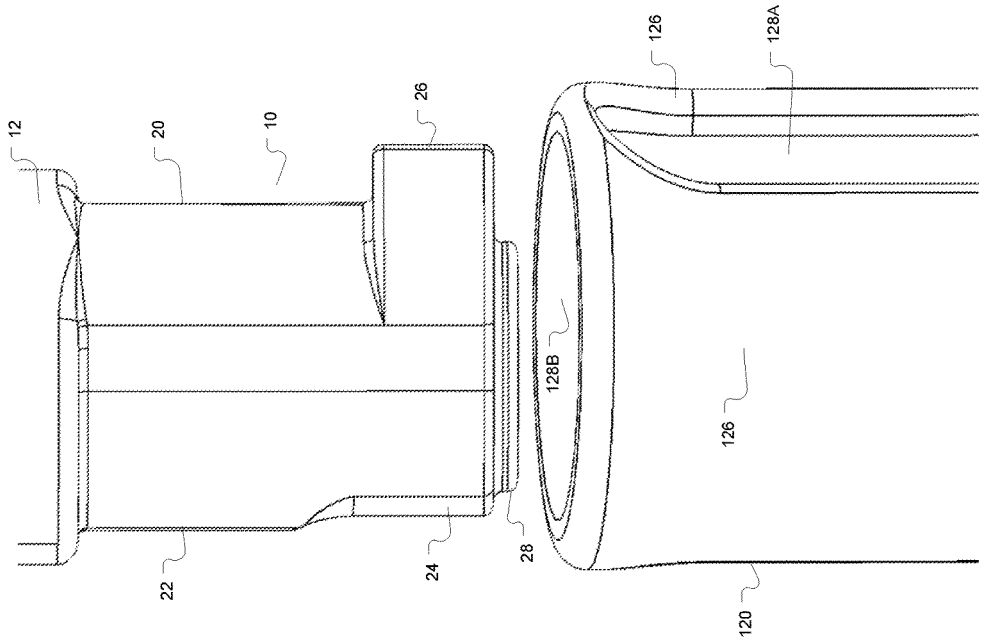
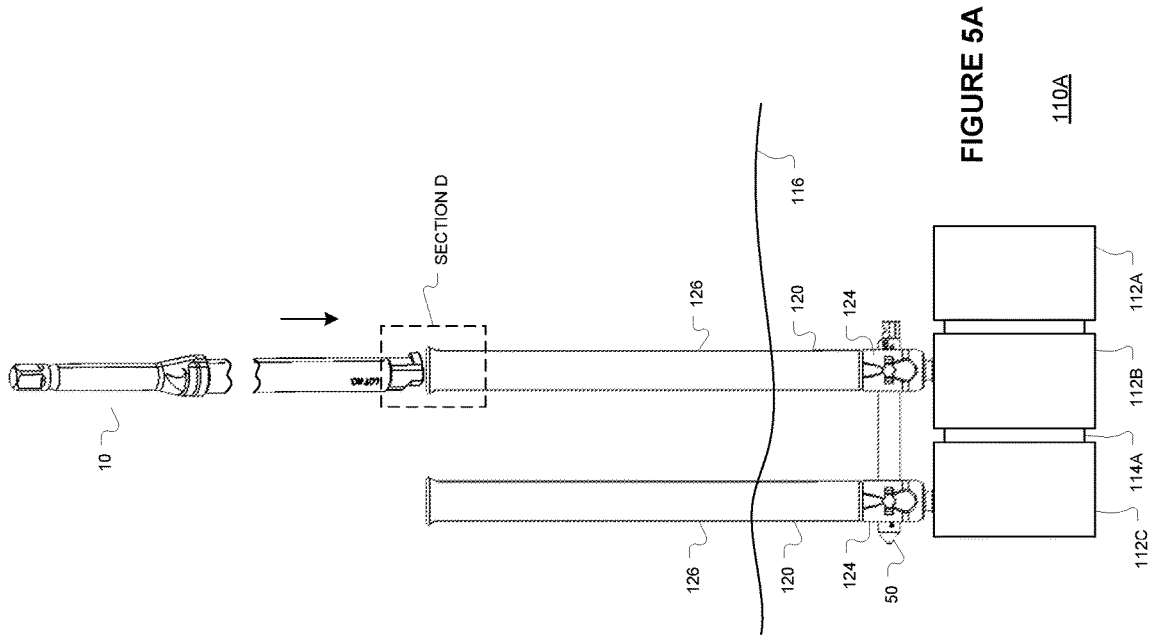
FIGURE 5B
FIGURE 5A

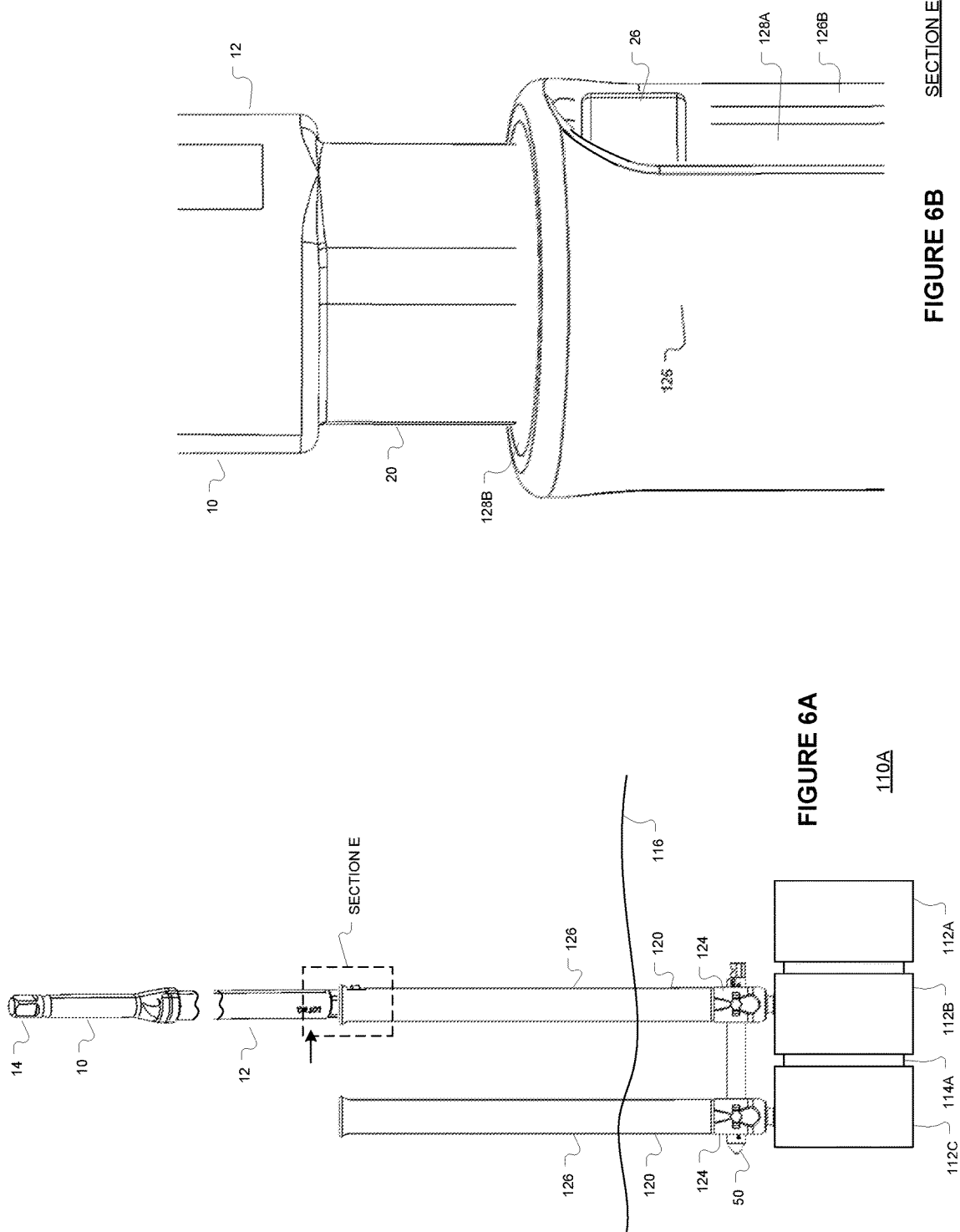

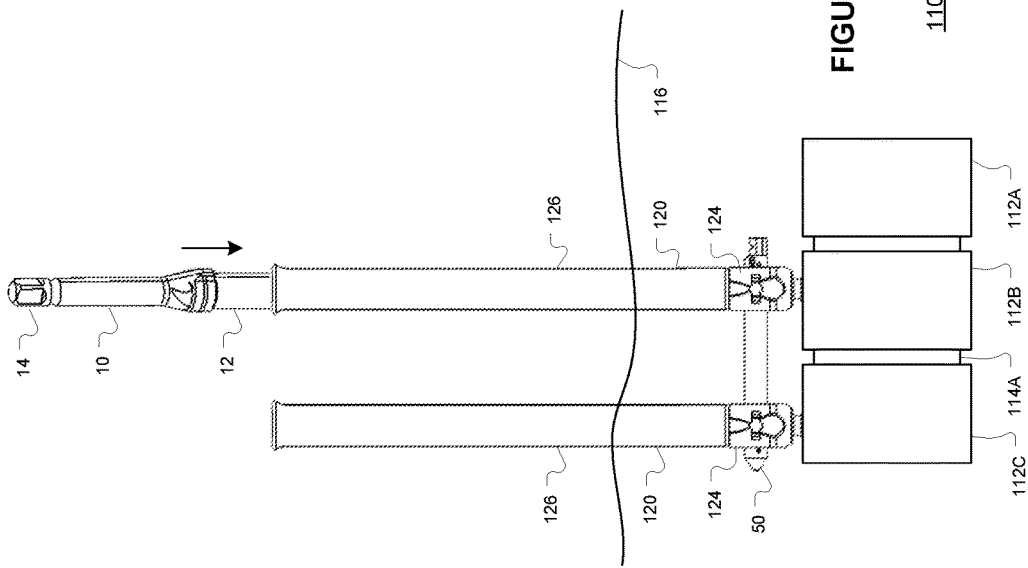
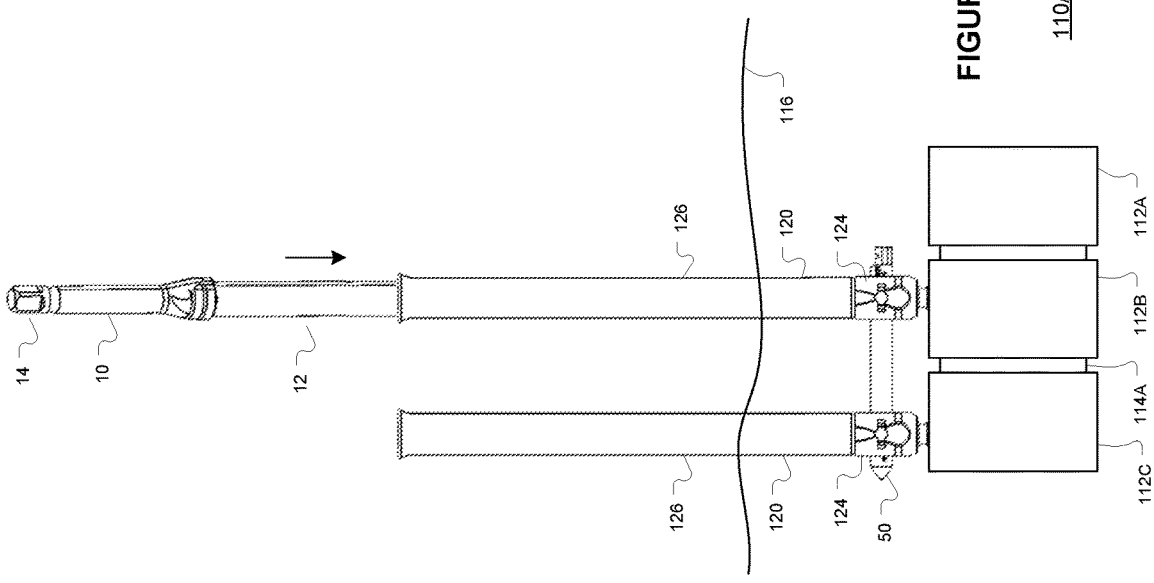

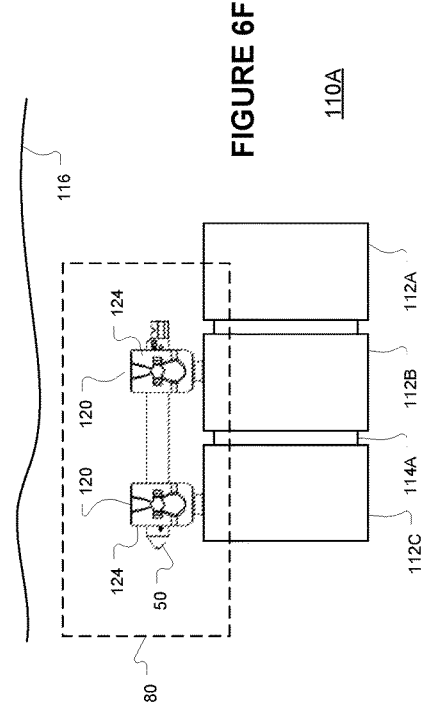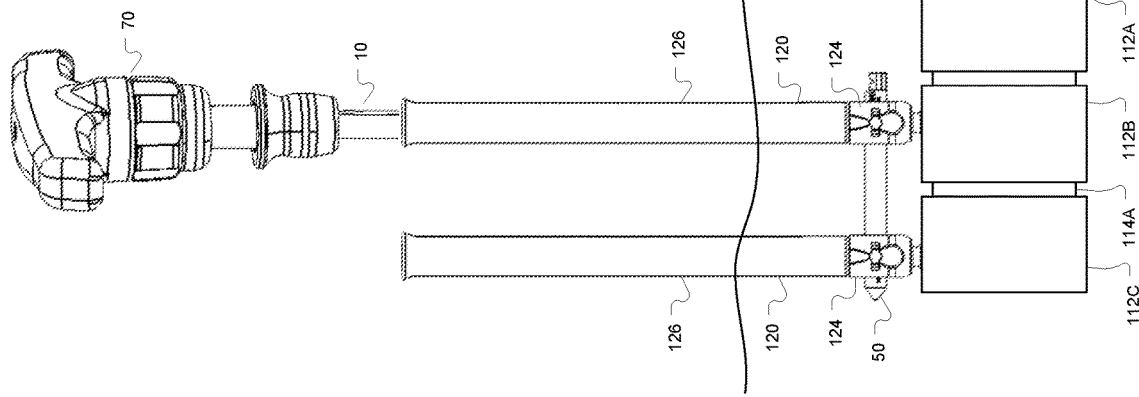

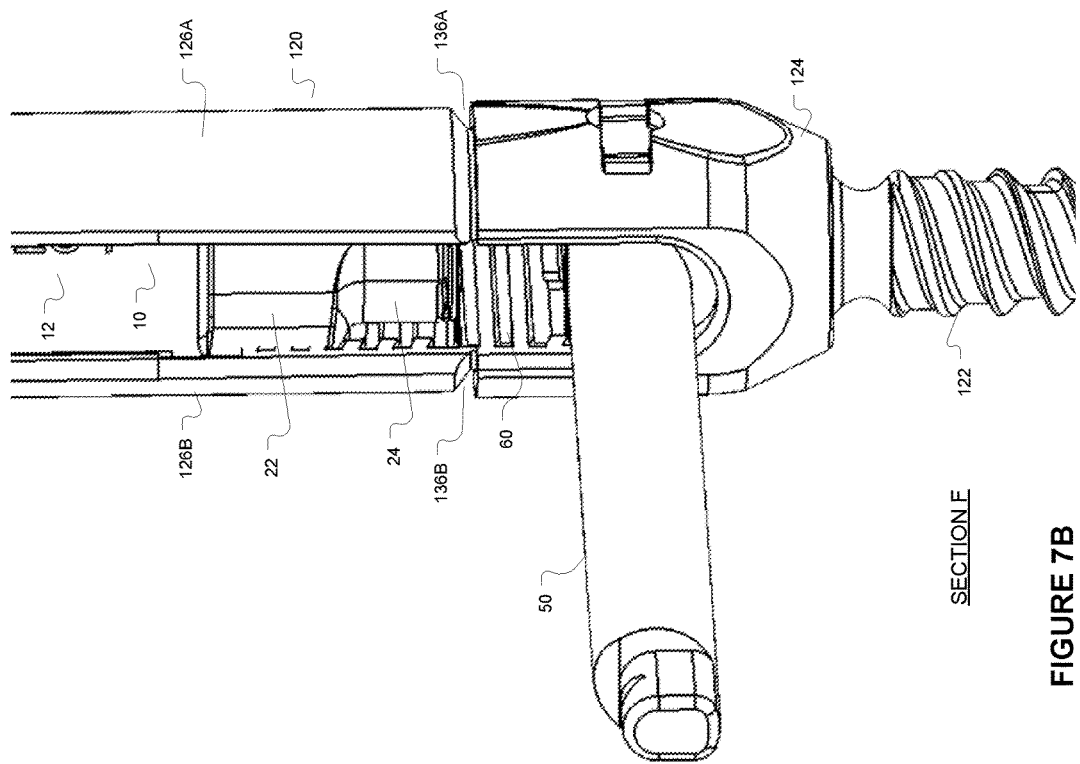
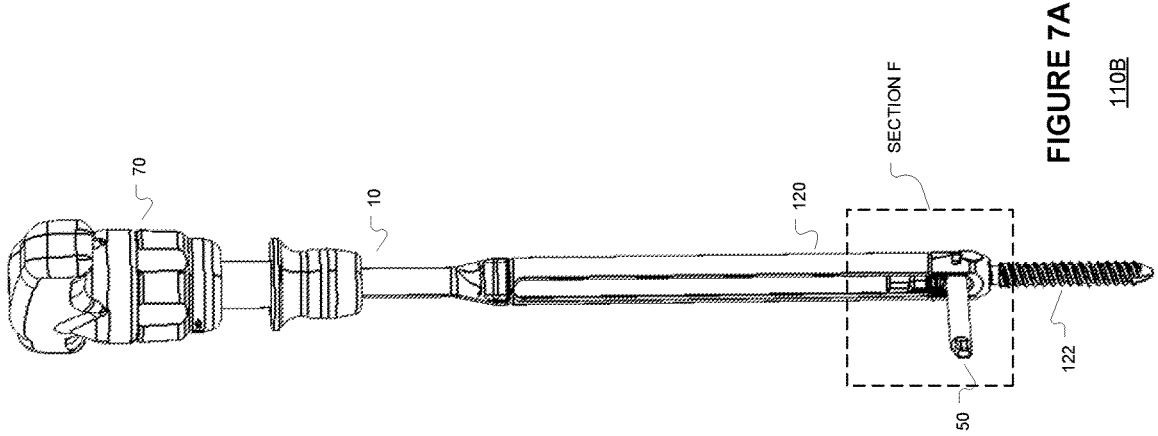
FIGURE 7B
FIGURE 7A

METHOD, SYSTEM, AND APPARATUS FOR BREAKING BONY SEGMENT IMPLANT EXTENSION

CROSS REFERENCE TO RELATED APPLICATIONS

This application is related to U.S. Provisional Application No. 62/261,404, filed Dec. 1, 2015, entitled "METHOD, SYSTEM, AND APPARATUS FOR BREAKING BONY SEGMENT IMPLANT EXTENSION", which is incorporated by reference herein.

TECHNICAL FIELD

Various embodiments described herein relate generally to bony segment implants including extensions designed to be broken away from the bony segment implant after placement at a desired location.

BACKGROUND INFORMATION

It may be desirable to enable a surgeon to break a section of a bony segment implant extension located in a transdermal location within a patient, the present invention provides system, apparatus, and methods for same. bony segment implant

BRIEF DESCRIPTION OF THE DRAWINGS

FIG. 1A is an isometric diagram of a bony segment implant extension arm breakage tool according to various embodiments.

FIG. 1B is an enlarged diagram of section A of bony segment implant extension arm breakage tool shown in FIG. 1A according to various embodiments.

FIG. 2A is another isometric diagram of a bony segment implant extension arm breakage tool according to various embodiments.

FIG. 2B is an enlarged diagram of section B of bony segment implant extension arm breakage tool shown in FIG. 2A according to various embodiments.

FIG. 4A is a partial, front isometric diagram of a bony segment implant extension arm breakage tool according to various embodiments.

FIG. 4B is an enlarged top view diagram of partial bony segment implant extension arm breakage tool shown in FIG. 3A according to various embodiments.

FIG. 4C is an enlarged bottom view diagram of partial bony segment implant extension arm breakage tool shown in FIG. 4A according to various embodiments.

FIG. 5A is a simplified posterior diagram of a bony segment implant extension arm breakage tool being initially inserted into an extension of a first mammalian bony segment implant coupled to a mammalian bony segment according to various embodiments.

FIG. 5B is an enlarged diagram of section D of a bony segment implant extension arm breakage tool being inserted into an extension of a first mammalian bony segment implant shown in FIG. 5A according to various embodiments.

FIG. 6A is a simplified posterior diagram of a bony segment implant extension arm breakage tool being shifted to be further inserted into an extension of a first mammalian bony segment implant coupled to a mammalian bony according to various embodiments.

FIG. 6B is an enlarged diagram of section E of a bony segment implant extension arm breakage tool being shifted to be further inserted an extension of a first mammalian bony segment implant shown in FIG. 6A according to various embodiments.

FIGS. 6C and 6D are simplified posterior diagrams of a bony segment implant extension arm breakage tool being further inserted into an extension of a first mammalian bony segment implant coupled to a mammalian bony segment according to various embodiments.

FIG. 6E is a simplified posterior diagram of a bony segment implant extension arm breakage tool fully inserted into an extension of a first mammalian bony segment implant coupled to a mammalian bony segment and being rotated via another tool to break an arm of the bony segment according to various embodiments.

FIG. 6F is a simplified posterior diagram of a construct formed in plurality of mammalian bony segments with extensions removed according to various embodiments.

FIG. 7A is a simplified front side view diagram of a bony segment implant extension arm breakage tool fully inserted into an extension of a first mammalian bony segment implant and being rotated via another tool to break an arm of the bony segment according to various embodiments.

FIG. 7B is an enlarged diagram of section F of a bony segment implant extension arm breakage tool fully inserted into an extension of a first mammalian bony segment implant and being rotated via another tool to break an arm of the bony segment according to various embodiments.

DETAILED DESCRIPTION

Figure 3B:
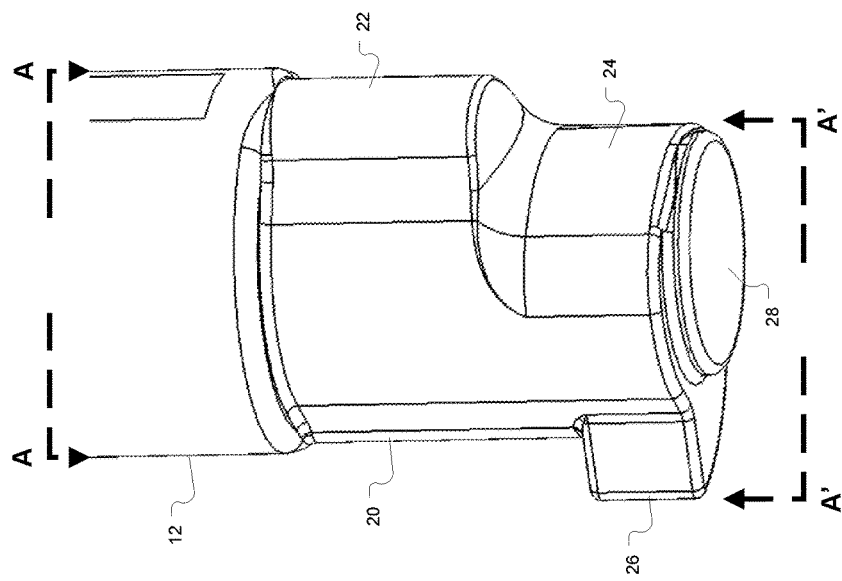
FIG. 3B is an enlarged diagram of section C of bony segment implant extension arm breakage tool shown in FIG. 3A according to various embodiments.

A medical practitioner including a surgeon may want to couple two or more bony segments (spine vertebrae in an embodiment 112A-C in FIG. 5A). A surgeon may insert mammalian bony segment implants (screws 120 FIG. 7) into one or more bony segments as part of a procedure. In an embodiment, a surgeon may want to place an implant into a bony segment via a minimum skin incision termed minimally invasive surgery (MIS). In such an embodiment, a surgeon may want to employ an implant 120 including a breakaway extension 126 that is sized to extend through a patient's skin (116 FIG. 5A) when initially implanted into a bony segment (FIG. 5A). Once the implant is placed and any constructs (if any) formed between other implants (such as via a rod 50 as shown in FIG. 5A), the implant extensions 126 may be desirably removed as shown in FIG. 6F leaving the implants 120 or construct subcutaneous to the patient's skin 116 in an embodiment.

Figure 9:
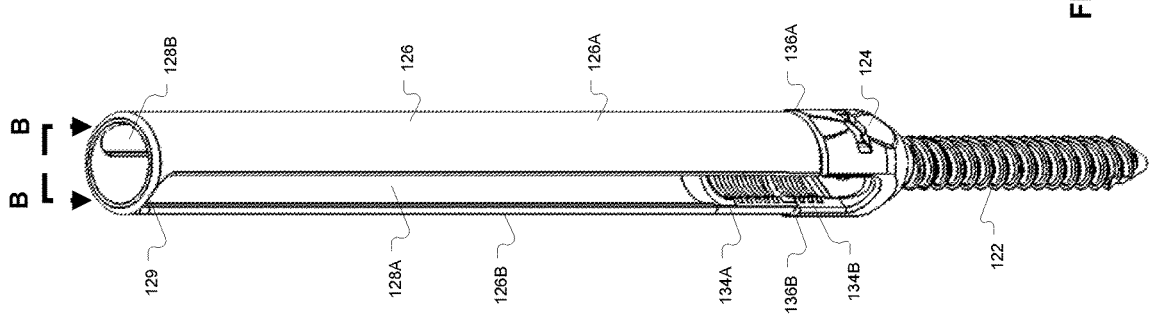
FIG. 9 is an isometric diagram of a mammalian bony segment implant with an extension according to various embodiments.

FIG. 9 is an isometric diagram of a mammalian bony segment implant 120 with a breakaway extension 126 including two arms 126A, 126B according to various embodiments. In an embodiment as shown in FIG. 9, an implant 120 may include a screw shaft 122, receiver 124, and a removable breakable extension 126. In an embodiment, the implant 120 may be minimally invasive surgery (MIS) pedicle screw (shaft 122 and receiver 124 forming a pedicle screw 120) and a breakaway extension 120 including arms 126A, 126B. A shown in FIG. 9, the extension 126 may include a first breakaway arm 126A, a second breakaway arm 126B, and extension couplings 129. Each arm 126A, 126B of the extension 126 may include driver and cap threads 134A.

The implant 120 may include a receiver 124 with threads 134B. for seating a rod 50 to a shaft 122 via a cap 60 with mating threads. Similar to the receiver 124, each extension arm 126A, 126B may include threads 134A that may be configured to be matingly coupled with a cap (60 FIG. 8B) or implant insertion driver. An implant insertion driver may be employed to insert an implant 120 into a bony segment 112A-C or remove an implant 120 from a bony segment 112A-C. The extension 126 arms 126A, 126B may be detactably coupled to the screw receiver 124 via reduced thickness or strength points 136A, 136B.

In an embodiment, the extension 126 may have a length of about 70 to 110 mm, an outer diameter of about 10-15 mm, an inner diameter of about 8-13 mm, and the threads 134A may start about 50-90 mm from the extension 136 proximal end 139 or have a length of about 8-15 mm. The extension 126 openings 128A, 128B may have a width greater than 6 mm when the rod 50 have a diameter of about 6.0 mm to enable the rod 50 to pass there through. The threads 134A, 134B may have a thread diameter of about 8 to 9 mm in an embodiment. In an embodiment the screw shaft 122 may have different lengths and diameters from 4.0 mm to 8.5 mm in diameter and 20 mm to 70 mm in length for use in pedicle implantation.

As shown in FIG. 5A, several implants 120 may be inserted into one or more bony segments 112A to 112C. In the embodiment 110A, shown in FIG. 5A, a first bony segment implant 120 may be inserted into a first bony segment 112C. A second bony segment implant 120 may be inserted into a second bony segment 112B. The bony segments 112C, 112B may be adjacent or separated by another bony segment 112A or body segment including a disc space or nucleus 114A. In an embodiment, a bony segment may be a vertebrae and the implants 120 may be pedicle screw implants.

The openings 128A, 128B of one or more implants 120 may be substantially aligned, the receiver 124 may rotatably and angularly move about a screw shaft 122 spherical head. In an embodiment, a rod may be desirably span two or more implants 120 and be fixably seated in the implants 120 receiver 124 rod saddle 138 via a cap 60. The implants 120 inserted into vertebrae 112C, 112B and rod spanning the implants 120 may form a construct 80 in an embodiment.

Once an implant 120 is inserted into a desired bony segment or construct 80 formed, the extension(s) 126 may be ideally removed. An extension breakaway apparatus 10 shown in FIGS. 1A-4C may be employed break an extension arm 126A-B in an embodiment.

FIG. 1A is an isometric diagram of a bony segment implant extension arm breakage tool or apparatus 10 according to various embodiments. FIG. 1B is an enlarged diagram of section A of a bony segment implant extension arm breakage apparatus shown in FIG. 1A according to various embodiments. As shown in FIGS. 1A and 1B, the apparatus 10 may have a distal end 20 coupled to a tool interface 14 via an elongated shaft 12 with diameter AA. The apparatus 10 may also include a shaft guard 16 located between the elongated shaft and the tool interface 14. As shown in FIG. 1B, the apparatus 10 distal end 20 may include cam 22, an inset 24 from the cam 22 and protruding curved fin 26. The distal end 20 inset 24 and curved fin 26 may have a distance or maximum diameter A'A'. In an embodiment, the diameter A'A' may be less than or about equal to the diameter AA.

As noted, an implant 120 may have an extension 126 with arms 126A, 126B forming openings or windows 128A down the vertical sides and a top opening 128B. The top opening 128B may have a known diameter in an embodiment greater than the diameters AA and A'A'. The top opening 128B may be circular in an embodiment. The top opening 128B may have a minimum diameter BB. In an embodiment, AA and A'A' may be less than BB to enable the extension breakaway apparatus 10 distal end 20 to be inserted into the implant extension 126 opening 128B as shown in FIG. 5B and then shifted so the fin 26 protrudes into a window 128A, 128B formed between the arms 126A, 126B as shown in FIG. 6B.

Figure 8B:
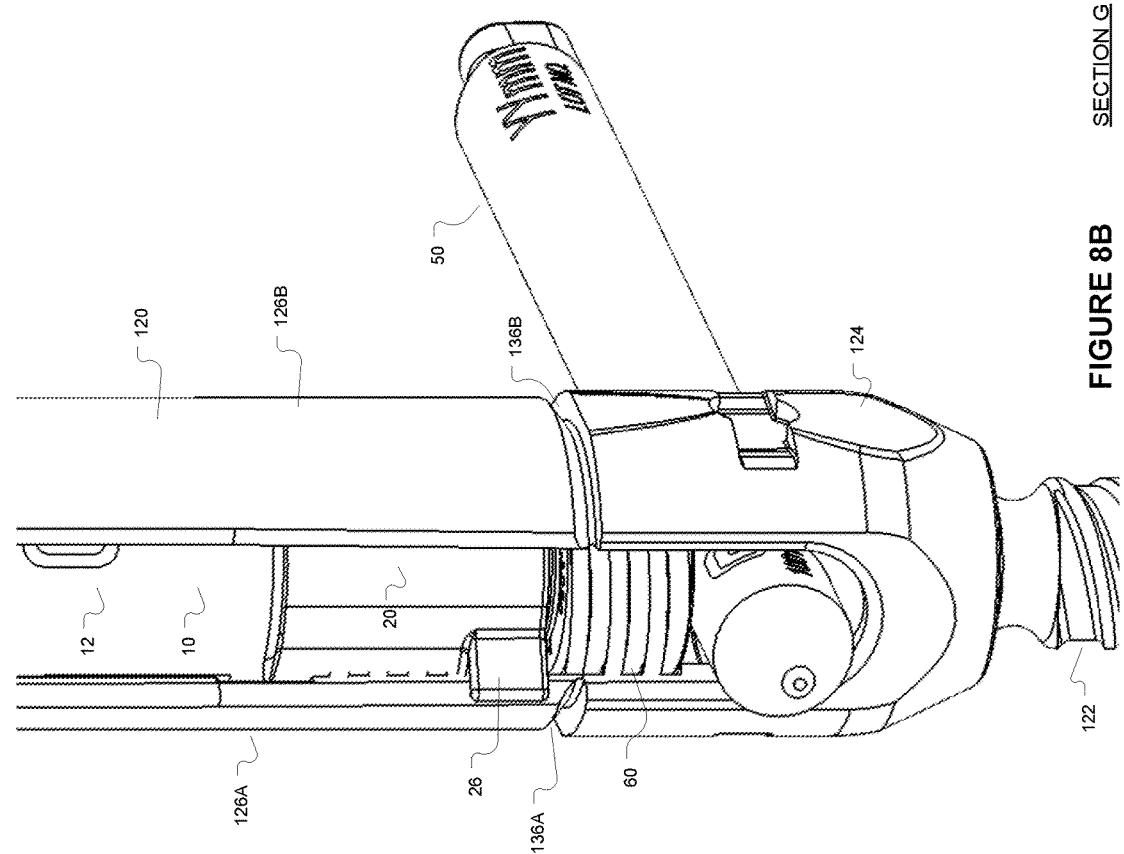
FIG. 8B is an enlarged diagram of section G of a bony segment implant extension arm breakage tool fully inserted into an extension of a first mammalian bony segment implant and being rotated via another tool to break an arm of the bony segment according to various embodiments.

Then the apparatus 10 distal end 20 and shaft 12 may be inserted into the bony implant 120 extension 126 until the distal end 20 tip 28 abuts the cap 60 as shown in FIGS. 6C, 6D, 6E, 7A, 7B, 8A, and 8B. Then the extension breakaway apparatus 10 may be coupled to another tool 70 and rotated clockwise (in an embodiment) to engage an extension arm 126A or 126B (as shown in FIG. 8B) to cause the arm 126A to breakaway or separate from the implant 120 receiver 124. In an embodiment the fin 126 is curved to enable the fin 136 to move within the extension 126 and then apply more pressure against an extension arm 126A, 126B until the extension arm 126A, 126B separates or breaks away from the implant 120 receiver 124.

As noted, extension 126 arms 126A, 126B may have reduced thickness or strength points 136A, 136B adjacent the implant rod and cap receiver 124. In an embodiment the length between the distal end 20 engaging tip (28 FIG. 3B) and the shaft guard 16 may be at least the length from the extension 126 opening 128B and the reduced thickness or strength points 136A, 136B to enable the curved fin 26 to be placed adjacent an extension 126 arm 126A, 126B via a window 128A formed between the arms 126A, 126B as shown in FIG. 6B.

Figure 3A:
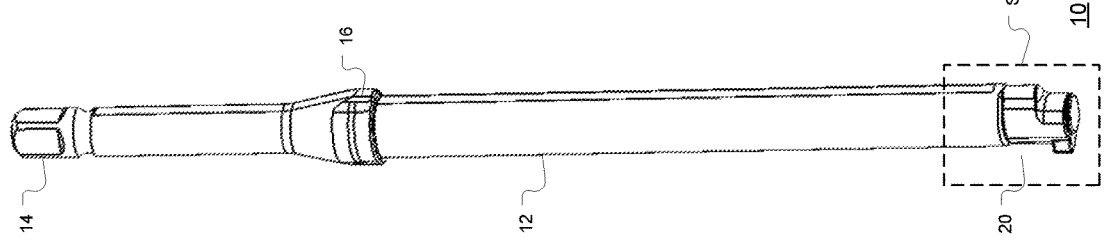
FIG. 3A is a front isometric diagram of a bony segment implant extension arm breakage tool according to various embodiments.

FIG. 2A is another isometric diagram of a bony segment implant extension arm breakage tool 10 according to various embodiments. FIG. 2B is an enlarged diagram of section B of bony segment implant extension arm breakage tool 10 shown in FIG. 2A according to various embodiments. FIG. 3A is a front isometric diagram of a bony segment implant extension arm breakage tool 10 according to various embodiments. FIG. 3B is an enlarged diagram of section C of bony segment implant extension arm breakage tool 10 shown in FIG. 3A according to various embodiments.

As shown in FIG. 3B, the tool 10 distal extension engaging end 20 may include a tip 28. The tip 28 may be sized and shaped to rest against a cap 60 in an implant 120 receiver 124. As also shown in FIG. 3B, the largest diameter about the cam 22 may also be about AA or A'A' where the center of the largest diameter of the cam section 22 may coincide axially with the elongated central shaft 12 center. The center of the largest diameter A'A' formed by the fin 26 and inset 24, however is offset laterally from the center of the largest diameter about the cam 22 and the center of the elongated central shaft 12 in an embodiment. FIG. 3C is an enlarged top view diagram of bony segment implant extension arm breakage tool 10 shown in FIG. 3A according to various embodiments.

Figure 3D:
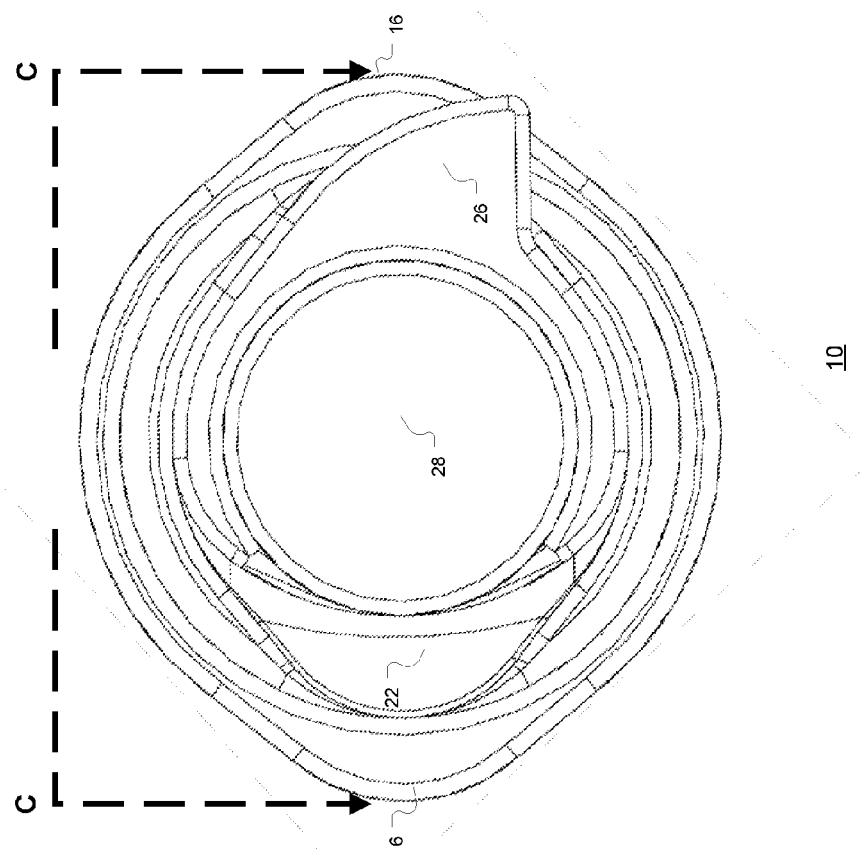
FIG. 3D is an enlarged bottom view diagram of bony segment implant extension arm breakage tool shown in FIG. 3A according to various embodiments.
Figure 3C:
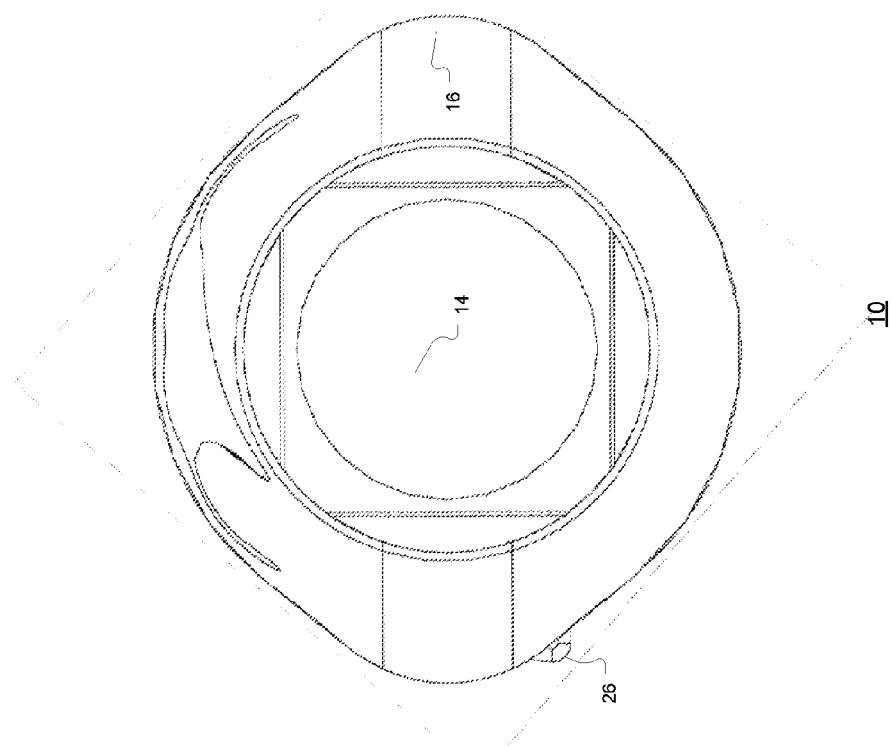
FIG. 3C is an enlarged top view diagram of bony segment implant extension arm breakage tool shown in FIG. 3A according to various embodiments.

FIG. 3D is an enlarged bottom view diagram of bony segment implant extension arm breakage tool 10 shown in FIG. 3A according to various embodiments. As shown in FIG. 3D, the largest outer diameter CC formed by the shaft guard 16 is larger than the diameters AA and A'A'. In an embodiment, the shaft guard 16 largest diameter CC is larger than the implant 120 extension opening 128B diameter BB. In an embodiment, the apparatus 10 distal end 20 and elongated section 12 may be about the length of the extension 126 so that when the apparatus 10 guard 16 rests against the extension 126 opening 128B, the apparatus 10 tip 28 abuts a construct 80 cap 60 seated in a receiver 124.

FIG. 4A is a partial, front isometric diagram of a bony segment implant extension arm breakage tool 10 according to various embodiments. FIG. 4B is an enlarged top view diagram of partial bony segment implant extension arm breakage tool 10 shown in FIG. 3A according to various embodiments. FIG. 4C is an enlarged bottom view diagram of partial bony segment implant extension arm breakage tool 10 shown in FIG. 4A according to various embodiments. As shown in FIGS. 4B and 4C, the apparatus 10 cam 22 largest diameter does not extend between the elongated central shaft 12 diameter. The fin 26, however does extend beyond the elongated central shaft 12 diameter.

Figure 10:
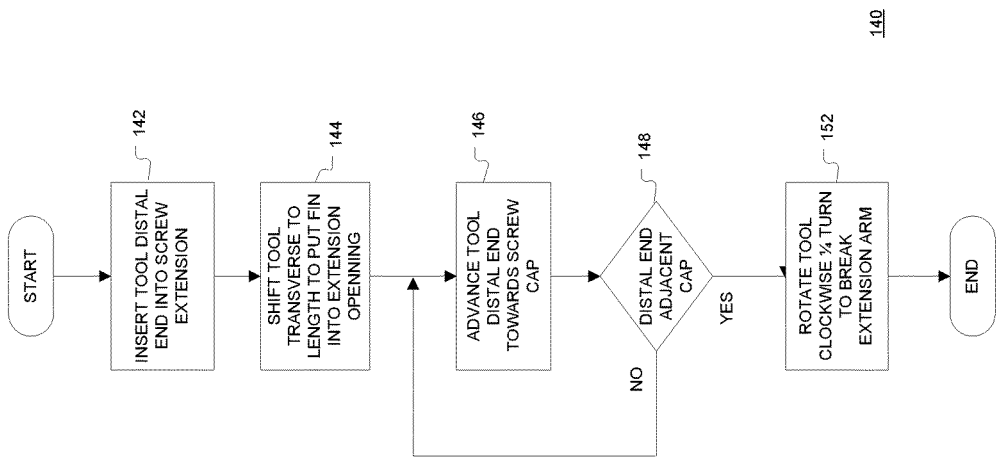
FIG. 10 is a flow diagram illustrating mammalian bony segment implant extension arm breakage via a breakage tool algorithms according to various embodiments.

FIG. 10 is an algorithm 140 for employing a bony segment implant extension arm breakoff apparatus 10 to separate an extension arm 126A, 126B of an extension 126 from an implant 120 receiver 124 according to various embodiments. In an embodiment, a bony segment implant extension arm breakage apparatus 10 distal end 20 fin 26 may be inserted into an extension opening 128B as shown in FIGS. 5A and 5B (activity 142). As shown in FIG. 5B the center of the largest diameter formed by the fin 26 and cam 24 may be aligned axially with the extension 126 opening 128B. Such alignment may enable the tool 10 distal end 20 fin 26 to pass into the extension 126 as shown in FIGS. 6A and 6B and enable the shaft 12 to be inserted into extension 126 by shifting the distal end laterally to cause the fin 26 to protrude into an opening 128A (activity 144).

FIG. 6B is an enlarged diagram of section E of a bony segment implant extension arm breakage tool 10 being shifted to be further inserted in an extension 126 of a first mammalian bony segment implant 120 shown in FIG. 6A according to various embodiments. FIGS. 6C and 6D are simplified posterior diagrams of a bony segment implant extension arm breakage tool 10 distal end 20 being further inserted into an extension 126 of a first mammalian bony segment implant 120 coupled to a mammalian bony segment 112B according to various embodiments. In an embodiment, a bony segment implant extension arm breakage apparatus 10 distal end 20 may be advanced (FIGS. 6C, 6D, 6E) into the extension 126 until the distal end 20 engaging tip 28 abuts the cap 60 as shown in FIGS. 7A and 7B (activities 146, 148).

Figure 8A:
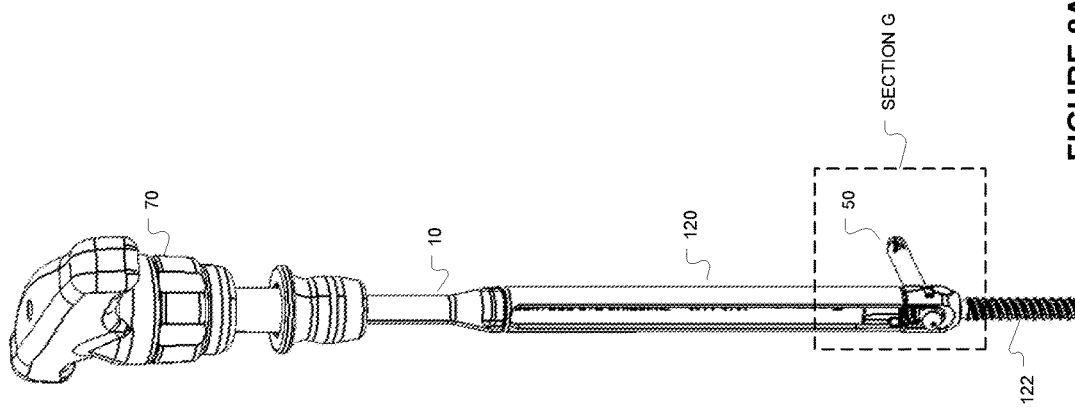
FIG. 8A is a simplified back side view diagram of a bony segment implant extension arm breakage tool fully inserted into an extension of a first mammalian bony segment implant and being rotated via another tool to break an arm of the bony segment according to various embodiments.

FIG. 6E is a simplified posterior diagram of a bony segment implant extension arm breakage tool 10 fully inserted into an extension 126 of a first mammalian bony segment implant 120 coupled to a mammalian bony segment 112B. FIG. 7A is a simplified front side view diagram of a bony segment implant extension arm breakage tool 10 fully inserted into an extension 126 of a first mammalian bony segment implant 120. FIG. 7B is an enlarged diagram of section F of a bony segment implant extension arm breakage tool 10 fully inserted into an extension 126 of a first mammalian bony segment implant 120. FIG. 8A is a simplified back side view diagram of a bony segment implant extension arm breakage tool 10 fully inserted into an extension 126 of a first mammalian bony segment implant 120 according to various embodiments. FIG. 8B is an enlarged diagram of section G of a bony segment implant extension arm breakage tool 10 distal end 20 fully inserted into an extension 126 of a first mammalian bony segment implant 120.

As shown in FIGS. 6E, 7A, 8A, another tool 70 may be removably coupled to the bony segment implant extension arm breakage tool 10 tool interface 14. The tool 70 may be a ratcheting tool in an embodiment. As shown in FIG. 7B, the bony segment implant extension arm breakage tool 10 distal end fin 26 may engage the base of an extension 126 arm 126A so that when the fin is rotated a ¼ turn clockwise may cause the extension arm 126A to break from receiver 124 at the break point 136A (activity 152). FIG. 7B shows the cam 22 biased against the extension 126 arm 126B threads 134A while the fin 26 engages the opposite arm 126A threads 134A. In an embodiment, once one arm of the two arms 126A, 126B is separated from the receiver 124, the other arm may be separated by hand. This process may be repeated for all implants of a construct 80 as shown in FIG. 6F.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A breakaway apparatus for breaking one of a plurality of elongated extensions of a bony implant, the bony implant including an elongated bony engaging segment having an axis, each of the plurality of elongated extensions having a length along the axis and coupled together at a proximal end to form an elongated opening between the plurality of elongated extensions from a distal end to the proximal end, the elongated opening having a minimum diameter along its length, the distal end of each of the plurality of elongated extensions breakably coupled to the elongated bony engaging segment, the breakaway apparatus comprising: an elongated shaft with a proximal section and a distal section, the shaft having a length along an axis from the proximal end to the distal end greater than the plurality of elongated extensions length, the elongated shaft proximal section having a maximum diameter less than the plurality of elongated extensions elongated opening minimum diameter, the elongated shaft distal section having a maximum diameter less than or about equal to the elongated shaft proximal section maximum diameter, the distal section having a central axis, the proximal section having a central axis, the distal section's central axis offset from the proximal section's central axis and the shaft distal section including a curved extension having an effective maximum diameter less than the plurality of elongated extensions opening minimum diameter to enable passage therethrough and sized to be able to engage the distal end of at least one of the plurality of elongated extensions and cause its decoupling from the elongated bony engaging segment when the curved extension is placed adjacent to the distal end and the breakaway apparatus is rotated about its shaft's axis.

2. The breakaway apparatus of claim 1, wherein the shaft distal section further includes a cam positioned opposite the curved extension and wherein the cam is sized to engage another of the plurality of elongated extensions above where the elongated extension is breakably coupled to the elongated bony engaging segment when the curved extension engages a distal end of one of the plurality of elongated extensions.

3. The breakaway apparatus of claim 2, wherein each of the plurality of elongated extensions include inner threads at the elongated extensions distal ends and the cam is sized to engage the inner threads of another of the plurality of elongated extensions above where the elongated extension is breakably coupled to the elongated bony engaging segment when the curved extension engages a distal end of one of the plurality of elongated extensions.

4. The breakaway apparatus of claim 2, wherein the bony implant includes a receiver breakably coupling the plurality of elongated extensions distal ends to the elongated bony engaging segment, the receiver configured to receive a cap, and the shaft distal section including a circular tip sized to engage a receiver cap when the curved extension engages a distal end of one of the plurality of elongated extensions.

5. The breakaway apparatus of claim 2, wherein the shaft proximal section includes a tool engaging interface.

6. The breakaway apparatus of claim 2, wherein the shaft proximal section is substantially circular along its axis.

7. The breakaway apparatus of claim 2, wherein the shaft proximal section is substantially circular and uniform along its axis.

8. The breakaway apparatus of claim 1, wherein the shaft proximal section includes an enlarged diameter section having a minimum diameter greater than the plurality of elongated extensions opening minimum diameter.

9. The breakaway apparatus of claim 1, wherein the shaft proximal section includes an enlarged diameter section having a minimum diameter greater than the plurality of elongated extensions opening minimum diameter and the shaft length between the proximal section and distal section sets the distal section curved section approximately adjacent the distal end of one of the plurality of elongated extensions when the enlarged diameter section engages the plurality of elongated extensions proximal end.

10. The breakaway apparatus of claim 1, wherein the bony implant includes a receiver breakably coupling the plurality of elongated extensions distal ends to the elongated bony engaging segment, the receiver configured to receive a cap, and the shaft distal section including a circular tip sized to engage a receiver cap when the curved extension is placed approximately adjacent to the distal end of the least one of the plurality of elongated extensions.

11. The breakaway apparatus of claim 1, wherein the shaft proximal section includes a tool engaging interface.

12. The breakaway apparatus of claim 1, wherein the shaft proximal section is substantially circular along its axis.

13. The breakaway apparatus of claim 1, wherein the shaft proximal section is substantially circular and uniform along axis.

* * * * *